(12) United States Patent
Pafumi et al.

(10) Patent No.: US 12,201,952 B2
(45) Date of Patent: Jan. 21, 2025

(54) DEVICES AND METHODS FOR DISPERSING A FIRST PHASE IN A SUBSTANTIALLY IMMISCIBLE CONTINUOUS PHASE

(71) Applicant: CAPSUM, Marseilles (FR)

(72) Inventors: Yan Eric Pafumi, Gardanne (FR); Mathieu Goutayer, Saint Malo (FR)

(73) Assignee: CAPSUM, Marseilles (FR)

( * ) Notice: Subject to any disclaimer, the term of this patent is extended or adjusted under 35 U.S.C. 154(b) by 1141 days.

(21) Appl. No.: 16/964,025

(22) PCT Filed: Jan. 24, 2019

(86) PCT No.: PCT/EP2019/051756
§ 371 (c)(1),
(2) Date: Jul. 22, 2020

(87) PCT Pub. No.: WO2019/145424
PCT Pub. Date: Aug. 1, 2019

(65) Prior Publication Data
US 2021/0039059 A1    Feb. 11, 2021

(30) Foreign Application Priority Data
Jan. 24, 2018  (FR) ..................... 18 50550

(51) Int. Cl.
*B01F 27/272*    (2022.01)
*A23L 33/00*    (2016.01)
(Continued)

(52) U.S. Cl.
CPC .............. *B01F 27/272* (2022.01); *A61K 9/10* (2013.01); *B01F 23/4105* (2022.01);
(Continued)

(58) Field of Classification Search
CPC ................ B01F 27/272; B01F 23/4105; B01F 35/71825; B01F 35/92; B01F 23/4144;
(Continued)

(56) References Cited

U.S. PATENT DOCUMENTS 2,798,698 A * 7/1957 Dooley ................. D01D 1/065
366/182.1
4,213,712 A * 7/1980 Aanonsen .......... B01F 25/3121
366/280
(Continued)

FOREIGN PATENT DOCUMENTS

DE    2814217 A1    10/1978
EP    3144058 A1    3/2017
(Continued)

OTHER PUBLICATIONS

Search Report for French Application No. FR 18 50550 dated Oct. 23, 2018.
Search Report for International Application No. PCT/EP2019/051756 dated Apr. 16, 2019.

*Primary Examiner* — Charles Cooley
(74) *Attorney, Agent, or Firm* — Pearne & Gordon LLP

(57) ABSTRACT

A device for producing a dispersion including elements including a first phase, which are dispersed in a continuous phase immiscible with the first phase is described herein. The device including at least one production nozzle including a first duct intended to convey a first fluid that forms the first phase, a second duct, coaxially surrounding part of the first duct, able to convey a second fluid that forms the continuous phase, and an outlet. The nozzle is able to form, at the outlet, a fluid jet including the first fluid and the second fluid surrounding the first fluid. The production device additionally includes a fragmentation device for mechanically breaking up the fluid jet, positioned in the vicinity of the outlet of the nozzle, the fragmentation device including (Continued)

a mobile part intended to break up the fluid jet mechanically into a plurality of elements.

2 Claims, 4 Drawing Sheets

(51) Int. Cl.
*A61K 9/10* (2006.01)
*B01F 23/41* (2022.01)
*B01F 35/71* (2022.01)
*B01F 35/90* (2022.01)
*B01F 35/92* (2022.01)
*B01J 13/08* (2006.01)
*B01J 13/10* (2006.01)

(52) U.S. Cl.
CPC ........ *B01F 35/71825* (2022.01); *B01F 35/92* (2022.01); *B01J 13/08* (2013.01); *B01J 13/10* (2013.01); *A23L 33/00* (2016.08); *A23V 2002/00* (2013.01); *B01F 23/4144* (2022.01); *B01F 23/4145* (2022.01); *B01F 2035/99* (2022.01); *B01F 2215/0431* (2013.01)

(58) Field of Classification Search
CPC .............. B01F 23/4145; B01F 2035/99; B01F 2215/0431; B01F 23/41; B01F 27/27; B01F 23/413; B01F 23/4143; B01F 23/43; B01F 33/80; A61K 9/10; B01J 13/08; B01J 13/10; A23L 33/00; A23V 2002/00; C11D 17/0017
USPC ........................................... 366/178.1–178.3
See application file for complete search history.

(56) References Cited

U.S. PATENT DOCUMENTS

| | | | | |
|---|---|---|---|---|
| 5,018,871 A | * | 5/1991 | Brazelton | B01F 27/1123 366/178.3 |
| 5,690,428 A | * | 11/1997 | Bryan | B01F 25/43231 239/432 |
| 6,659,636 B1 | * | 12/2003 | Matula | B01F 33/05 366/173.1 |
| 7,448,793 B2 | * | 11/2008 | Kurosawa | B01F 25/45211 366/172.2 |
| 8,079,752 B2 | * | 12/2011 | Rausch | B01F 33/811 366/181.4 |
| 8,491,848 B2 | * | 7/2013 | Gandhi | B01F 27/2711 422/224 |
| 8,602,634 B2 | * | 12/2013 | Matula | B01F 25/314 239/416.4 |
| 9,277,759 B2 | | 3/2016 | Bibette et al. | |
| 9,993,398 B2 | | 6/2018 | Goutayer et al. | |
| 10,300,006 B2 | | 5/2019 | Goutayer et al. | |
| 2002/0131325 A1 | * | 9/2002 | Matula | B01F 33/05 162/100 |
| 2007/0258315 A1 | * | 11/2007 | Matula | B01J 4/008 366/134 |
| 2014/0011033 A1 | * | 1/2014 | Carreras | A61K 9/4833 264/4.7 |
| 2017/0340548 A1 | | 11/2017 | Goutayer et al. | |
| 2019/0247811 A1 | * | 8/2019 | Bardon | B01F 23/4105 |
| 2021/0039059 A1 | * | 2/2021 | Pafumi | B01F 27/272 |

FOREIGN PATENT DOCUMENTS

| | | |
|---|---|---|
| FR | 3041251 A1 | 3/2017 |
| FR | 3063899 A1 | 9/2018 |
| WO | 2010063937 A1 | 6/2010 |
| WO | 2012120043 A2 | 9/2012 |
| WO | 2015055748 A1 | 4/2015 |
| WO | 2016096995 A1 | 6/2016 |

* cited by examiner

DEVICES AND METHODS FOR DISPERSING A FIRST PHASE IN A SUBSTANTIALLY IMMISCIBLE CONTINUOUS PHASE

CROSS-REFERENCE TO RELATED APPLICATIONS

This is a National Stage application of PCT international application PCT/EP2019/051756, filed on Jan. 24, 2019, which claims the priority of French Patent Application No. 18 50550, Jan. 24, 2018, both of which are incorporated herein by reference in their entirety.

FIELD OF THE INVENTION

The present invention relates to a device for producing a dispersion. The invention also relates to a production assembly comprising at least one such device as well as a method for producing a dispersion implementing such a device.

BACKGROUND OF THE INVENTION

The Applicant manufactures and markets macroscopic dispersions comprising elements that are visible to the eye, for example with a diameter of between 100 µm and 1500 µm, which are kinetically stable and optionally monodisperse.

The production of a dispersion comprising elements dispersed in a continuous phase, for example macro-emulsions, generally consists of performing a mixture between at least two phases that are substantially immiscible with respect to one another, either directly in the production vat, or in an in-line reactor.

Nevertheless, such methods make it very difficult, if not impossible, to obtain a homogeneous distribution of the dispersed elements in the continuous phase. It is also difficult to obtain high concentrations of dispersed phase, as well as to obtain macroscopic dispersed elements, in particular of millimetric or larger size, and/or of homogeneous size. These difficulties are further increased when one of the phases has a high viscosity, or when one wishes to obtain a fast production pace It is known to produce the elements of the dispersion in milli- or micro-fluidic devices, for example like that described in WO2012/120043, in order to precisely control their dimensions and the homogeneity of their distribution in the continuous phase. These devices can be further improved. Indeed, they do not make it possible to easily obtain fast production paces due to their hydrodynamic working, the separation of the elements using a process of the dripping type.

The fluids having to be able to flow in channels with a very small section, these milli- or micro-fluidic devices also impose limits in terms of viscosity or at least adaptations in terms of raw materials and/or devices. These drawbacks de facto limit the galenic aspects and/or the sensoriality of the dispersions that may be obtained and/or make the dispersion production method more complex.

BRIEF SUMMARY OF THE INVENTION

One aim of the invention is to provide a production device making it possible to obtain, easily and with higher production yields, dispersed elements, in particular macroscopic and if applicable monodisperse, and/or in a high concentration, even in the presence of at least one phase of high viscosity, while easily controlling the effects of the change of production scale.

Thus, the invention relates to a production device of the aforementioned type, characterized in that the dispersion comprising elements comprising at least one first phase, which are dispersed in a continuous phase substantially immiscible with the first phase, the device comprising:

at least one production nozzle comprising at least a first duct intended to convey a first fluid that forms the first phase, a second duct surrounding, preferably coaxially, at least part of the first duct, the second duct being able to convey a second fluid that forms the continuous phase, and an outlet, the nozzle being able to form, at the outlet, a fluid jet comprising at least the first fluid and the second fluid surrounding the first fluid, preferably coaxially, and at least one fragmentation device for mechanically breaking up the fluid jet, positioned in the vicinity of the outlet of the nozzle, the fragmentation device comprising a mobile part relative to the nozzle, intended to break up the fluid jet mechanically into a plurality of elements comprising the first fluid dispersed in the continuous phase.

According to specific embodiments, the device according to the invention has one or more of the following features, considered separately or according to any technically possible combination:

the mechanical fragmentation device is mobile with respect to the nozzle;

the production nozzle comprises a third duct, at least part of which is surrounded, preferably coaxially, by at least part of the first duct, the third duct being able to convey a third fluid that is substantially immiscible with the first fluid, the fluid jet comprising the third fluid, the first fluid surrounding the third fluid, preferably coaxially, and the second fluid surrounding the first fluid, preferably coaxially, each element dispersed in the continuous phase comprising an outer core formed by the first fluid, and at least one, preferably a single, inner core formed by the third fluid arranged in the outer core;

each element comprises a shell (or membrane), preferably formed by a coacervate layer, at the interface between the first phase and the continuous phase, and optionally further at the interface between the first phase and the third fluid when this third fluid is present;

the first phase of the elements forms a shell formed by a layer comprising at least one gelling agent, in particular chosen from a heat-sensitive gelling agent that is solid at ambient temperature and atmospheric pressure, a polysaccharide, in particular a polyelectrolyte reactive to multivalent ions, between the third fluid and the continuous phase;

the device comprises at least one independent duct intended to convey an additional fluid toward the dispersion comprising at least one solution for increasing the viscosity of the continuous phase;

the device comprises at least one heating device able to heat at least the first fluid, and optionally the second fluid and/or the third fluid, at least in the production nozzle;

the device comprises at least one cooling device able to cool the dispersion, in particular when the device comprises at least one heating device as described above;

the mobile part of the fragmentation device comprises a rotating or oscillating scraper, provided with successive openings;

the successive openings are able to pass successively across from the nozzle during the movement of the mobile part with respect to the nozzle;

the elements have a substantially spherical shape;

at least 60%, or even at least 70%, preferably at least 80%, and better still at least 90% of the elements have a mean diameter greater than or equal to 10 µm, preferably greater than or equal to 50 µm, in particular greater than or equal to 100 µm, or even greater than or equal to 200 µm, better still greater than or equal to 300 µm, in particular greater than or equal to 400 µm, and better still greater than or equal to 500 µm;

the first fluid and/or the second fluid and/or, when present, the third fluid, is not a gas; and the device further comprises at least one mixer able to exert a controlled homogeneous shear on the elements, preferably said mixer comprising at least one cell formed by at least:
two coaxial rotary cylinders;
two parallel rotary discs; or
two parallel oscillating plates.

According to one particular embodiment, in order to improve the monodispersity of the elements, the elements undergo a size refining step during which they are subject to a shear capable of fragmenting them into elements of homogeneous and controlled diameters. Preferably, the refining step is carried out in a high-shear cell of the Couette type, according to a method described in document EP 3,144,058.

The invention also relates to an assembly for producing a dispersion comprising a plurality of production devices as described above, and a fluid distribution system able to supply each device at least with first fluid and second fluid and, optionally, with third fluid, preferably the outlets of the nozzles emerging in a same chamber.

According to specific embodiments, the assembly according to the invention has one or more of the following features, considered separately or according to any technically possible combination:

the devices are positioned along at least one centripetal circle, the outlets of the nozzles being oriented toward a center of the circle;

the devices are positioned along at least one centrifugal circle, the outlets of the nozzles being oriented toward the outside of the circle;

the devices are positioned along at least one circle, the outlets of the nozzles being parallel to one another;

the fragmentation device is shared by all of the devices;

the mobile part of the shared fragmentation device comprises a rotating or oscillating scraper arranged to travel an inner contour of the centripetal circle;

the mobile part of the shared fragmentation device comprises a rotating or oscillating scraper arranged to travel an outer contour of the centrifugal circle; and the mobile part of the shared fragmentation device comprises a rotating or oscillating scraper arranged to come opposite the outlets of the nozzles parallel to one another.

The invention further relates to a method for manufacturing a dispersion comprising elements comprising at least a first phase dispersed in a continuous phase, the method comprising at least the following steps:

providing a production device as described above and at least a first fluid and a second fluid that is substantially immiscible with the first fluid;

pouring the first fluid in the first duct, the first fluid forming the first phase and the second fluid in the second duct surrounding, preferably coaxially, the first duct;

forming a fluid jet at the outlet of the nozzle, the fluid jet, formed by coextrusion, comprising at least the first fluid and the second fluid surrounding the first fluid, preferably coaxially;

moving the mobile part of the fragmentation device in order to split the fluid jet and obtain elements comprising at least the first fluid dispersed in the second fluid; and recovering the dispersion.

According to specific embodiments, the method according to the invention has one or more of the following features, considered separately or according to any technically possible combination:

the method comprises a step for pouring a third fluid in a third duct, at least part of the third duct being surrounded, preferably coaxially, by at least a part of the first duct, the fluid jet also comprising the third fluid, the first fluid surrounding the third fluid, preferably coaxially; and the method comprises a size refining step, during which a controlled and homogeneous shear is applied to the elements in a mixer, the mixer in particular being of the Couette type, comprising two coaxial cylinders, an outer cylinder with inner radius $R_o$ and an inner cylinder with outer radius $R_i$, the outer cylinder being stationary and the inner cylinder rotating with an angular speed $\omega$.

According to one particular embodiment, the phases of the dispersion form a macroscopically inhomogeneous mixture. This is notably the case when the dispersed elements have a macroscopic nature.

In the context of the present invention, the aforementioned dispersions can be referred to interchangeably as "emulsions."

According to one embodiment, the dispersions according to the invention do not comprise a surfactant.

The invention lastly relates to a composition, in particular cosmetic, comprising at least one dispersion as described above, and optionally, a physiologically acceptable medium.

BRIEF DESCRIPTION OF THE DRAWINGS

The invention will be better understood upon reading the following description, provided solely as an example and done in reference to the appended drawings, in which.

DESCRIPTION OF EXAMPLE EMBODIMENTS

Temperature and Pressure

Unless otherwise indicated, hereinafter, it is considered that one is at ambient temperature (for example T=25° C.±2° C.) and atmospheric pressure (760 mm of Hg, or $1.013 \cdot 10^5$ Pa or 1013 mbar).

Viscosity

The viscosity of the dispersions according to the invention may vary significantly, which makes it possible to obtain varied textures.

According to one embodiment, each of the phases forming a dispersion according to the invention and/or the dispersion according to the invention has a viscosity ranging from 1 mPa·s to 500,000 mPa·s, preferably from 10 mPa·s to 300,000 mPa·s, preferably from 400 mPa·s to 200,000 mPa·s, in particular from 1,000 mPa·s to 100,000 mPa·s, and more specifically from 2000 mPa·s to 150,000 mPa·s, or from 2,000 mPa·s to 10,000 mPa·s, as measured at 25° C.

The viscosity is measured at ambient temperature, for example T=25° C.+/−2° C., and at ambient pressure, for example 1013 mbar, using the following method.

Figure 1:
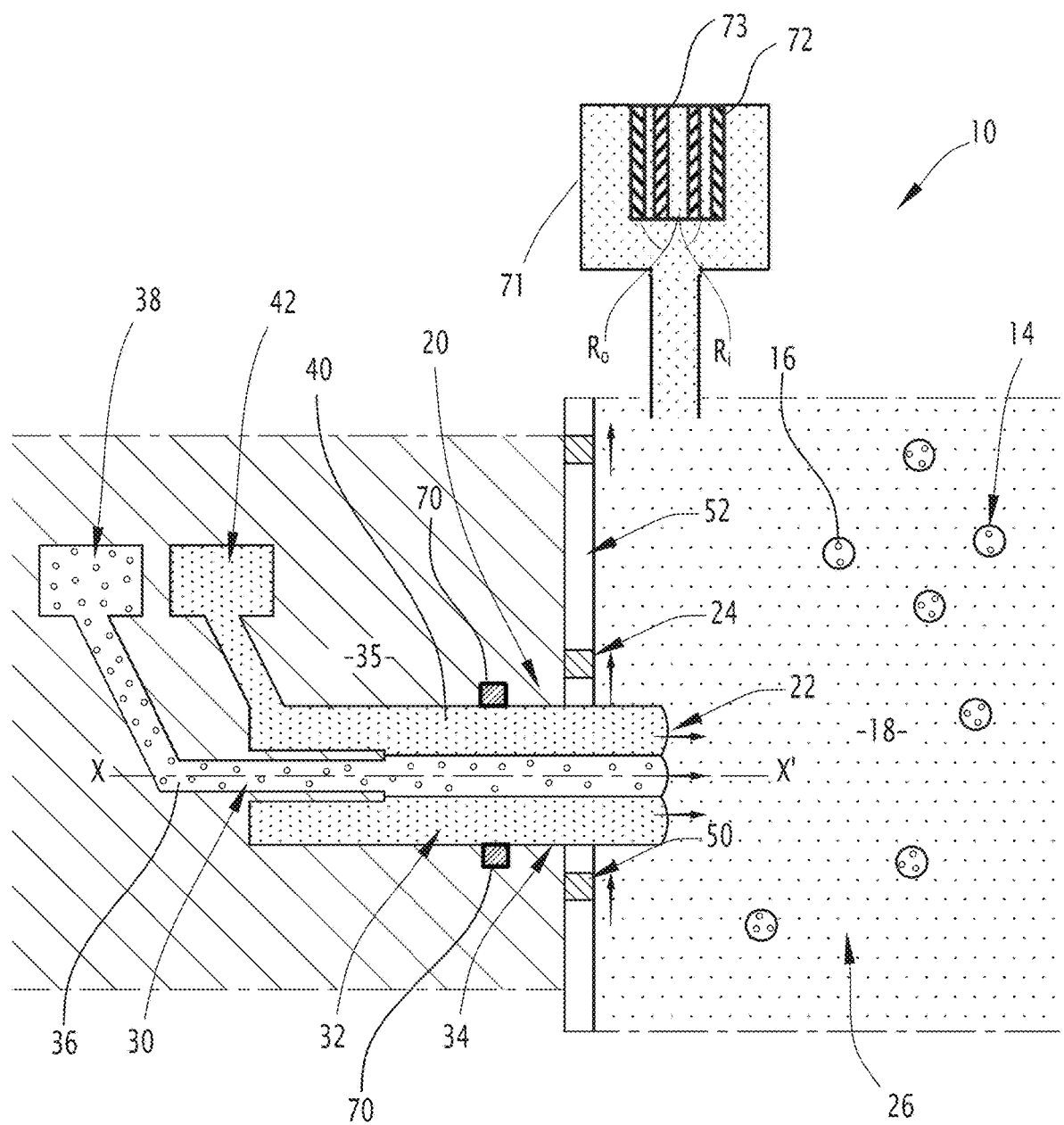
FIG. 1 is a schematic longitudinal sectional view of a production device according to the invention.

In reference to FIG. 1, a device 10 is described for producing a dispersion 12 according to a first embodiment of the invention, the dispersion 12 comprising elements 14 comprising a first phase 16, dispersed in a continuous phase 18.

Dispersion 12

The dispersion 12 is direct (that is to say, oil-in-water type) or inverse (that is to say, water-in-oil type). The obtained dispersion 12 is kinetically stable. Within the meaning of the present invention, "kinetically stable" for example means that the dispersion is stable for at least two weeks, or even one month, preferably three months, and better still six months. "Stable" means that the dispersion retains a satisfactory visual homogeneity, that is to say, without phase shift or creaming perceptible to the naked eye, the absence of opacification of the continuous phase, absence of clumping of the elements with one another, and in particular the absence of coalescence or Ostwald ripening of the elements with respect to one another, and the absence of leaking of materials from the dispersed phase toward the continuous phase, or vice versa.

The first phase 16 is aqueous or oily, preferably oily, and immiscible with the continuous phase 18 at ambient temperature and atmospheric pressure.

Within the meaning of the present invention, "immiscible" or "substantially immiscible" is meant to designate the solubility of a first phase (or fluid) in a second phase (or fluid) that, at ambient temperature and atmospheric pressure, is advantageously less than or equal to 5% by weight.

The continuous phase 18 is oily or aqueous, preferably aqueous, and in particular different in nature from the first phase 16.

Oils usable in the present invention include those described in the patent application filed under no. FR1759183, the content of which is incorporated herein by reference.

The elements 14 are advantageously substantially spherical and preferably macroscopic.

Preferably, at least 60%, or even at least 70%, preferably at least 80%, and better still at least 90% of the elements 14 have a mean diameter D greater than or equal to 10 µm, preferably greater than or equal to 50 µm, in particular greater than or equal to 100 µm, or even greater than or equal to 200 µm, and better still greater than or equal to 300 µm, in particular greater than or equal to 400 µm, and better still greater than or equal to 500 µm. In particular, at least 60%, or even at least 70%, preferably at least 80%, and better still at least 90%, of the elements 14 have a mean diameter D of between 10 µm and 3,000 µm, in particular between 50 µm and 2,500 µm, preferably between 100 µm and 2,000 µm, in particular between 200 µm and 1,500 µm, or even between 500 µm and 1,000 µm.

Preferably, the elements 14 have a diameter greater than or equal to 100 µm, and represent a volume greater than or equal to 60%, or even greater than or equal to 70%, preferably greater than or equal to 80%, and better still greater than or equal to 90% of the total volume of the dispersed phase.

The elements 14 advantageously have an apparent monodispersity (that is to say, they are perceived by the eye as spheres of identical diameter).

"Apparent monodispersity" means, for a given population of elements 14, a variation coefficient Cv of the mean diameter $\overline{D}$ of the elements 14 of between 10% and 30%, and preferably between 15% and 20%.

The mean diameter $\overline{D}$ of the elements 14 is for example measured by analyzing a photograph of a lot made up of N elements 14, using image processing software. Typically, according to this method, the diameter is measured in pixels, then converted to µm, based on the size of the container containing the elements 14 of the dispersion 12.

Preferably, the value of N is chosen to be greater than or equal to 30, such that this analysis provides a statistically significant reflection of the diameter distribution of the elements of said emulsion. N is advantageously greater than or equal to 100, in particular in the case where the dispersion is polydispersed.

The diameter Di of each element 14 is measured, then the mean diameter $\overline{D}$ is obtained by calculating the arithmetic mean of these values:

$$\overline{D} = \frac{1}{N} \sum_{i=1}^{N} D_i$$

From these values Di, it is also possible to obtain the standard deviation σ of the diameters of the elements 14 of the dispersion 12:

$$\sigma = \sqrt{\frac{\sum_{i=1}^{N} (D_i - \overline{D})^2}{N}}$$

The standard deviation σ of a dispersion reflects the distribution of the diameters Di of the elements 14 of the dispersion 12 around the mean diameter $\overline{D}$.

By knowing the mean diameter $\overline{D}$ and the standard deviation σ of a Gaussian dispersion, it is possible to determine that 95.4% of the population of elements 14 is found in the interval of diameters [$\overline{D}-2\sigma$; $\overline{D}+2\sigma$] and 68.2% of the population is found in the interval [$\overline{D}-\sigma$; $\overline{D}+\sigma$].

In order to characterize the monodispersity of the dispersion 12 according to this embodiment of the invention, it is possible to calculate the variation coefficient:

$$C_v = \frac{\sigma}{D}$$

This parameter reflects the distribution of the diameters of the elements 14 as a function of the mean diameter thereof.

The variation coefficient Cv of the diameters of the elements 14 is advantageously less than 30%, preferably less than 20%, and more preferably less than 10%, or even less than 5%.

Alternatively, the monodispersity can be shown by placing a dispersion sample according to the invention in a vial with a constant circular section. Gentle agitation by rotating a quarter revolution over a half-second around the axis of symmetry crossing through the file, followed by rest for one half-second, is done, before repeating the operation in the opposite direction, four times in a row.

The elements of the dispersed phase organize themselves in a crystalline form when they are monodispersed. Thus, they have a stack following a pattern repeating in all three dimensions. It is then possible to observe a regular stack that indicates a good monodispersity, an irregular stack reflecting polydispersity of the dispersion 12. If applicable, one skilled in the art will know how to adjust the viscosity of the phases, in particular of the continuous phase 18, for a satisfactory implementation of this method of characterizing the monodispersity.

The dispersion 12 can advantageously comprise a fraction greater than or equal to 2%, preferably greater than or equal to 5%, better still greater than or equal to 10%, in particular greater than or equal to 15%, preferably greater than or equal to 20%, and in particular greater than or equal to 30% by weight of first phase 16, in particular oil(s), relative to the total weight of the dispersion 12. On the contrary, with a dripping method of the prior art, the maximal fraction in dispersed phase, in particular in oil(s), achievable by direct dispersion is about 15%.

Thus, the dispersion 12 can advantageously comprise a fraction of between 15% and 60%, preferably between 20% and 50%, in particular between 30% and 40%, by weight of first phase 16, in particular oil(s), relative to the total weight of the dispersion 12.

In the embodiment shown in FIG. 1, each element 14 of the dispersion is formed by a drop of first phase 16.

According to a variant embodiment, each element 14 of the dispersion may comprise at least one shell 16A. One skilled in the art will know how to make the necessary adaptations and/or adjustments to ensure that this shell 16A forms, while in particular taking account of the particularities of the device according to the invention.

For example, the shell 16A can be formed by a layer of coacervate at the interface between the first phase 16 and the continuous phase 18. This layer of coacervate is advantageously formed by interaction between at least a first precursor polymer of the coacervate initially contained in the first phase 16 and at least a second precursor polymer of the coacervate initially contained in the continuous phase 18. Thus, the first polymer is a hydrophilic polymer and the second precursor polymer is a lipophilic polymer, or vice versa. A "first precursor polymer of the coacervate/second precursor polymer of the coacervate" pair is in particular a "carbomer/amodimethicone" pair. Examples of elements of this type are described in WO2012120043, the content of which is incorporated by reference.

A device according to the invention is further advantageous in that it makes it possible to form a dispersion 12 by eliminating the implementation of an intermediary liquid generally implemented to delay the migration of one of the two polymers involved in the coacervation reaction toward the interface between the dispersed phase 16 and the continuous phase 18, without dirtying the nozzle.

According to a second variant (not shown), each element 14 of the dispersion 12 comprises at least one first gelling agent in the first phase 16 and optionally at least one second gelling agent in the continuous phase 18. In other words, the elements 14 of the dispersion 12 according to this second variant have an improved kinetic stability and mechanical resistance despite the absence of shell. The first phase 16 and/or the continuous phase 18 are for example gelled. Examples of hydrophilic or lipophilic gelling agents are described in the application filed under no. FR1752208, the content of which is incorporated by reference.

According to a third variant embodiment (not shown), the dispersion 12 comprises at least one first gelling agent in the first phase 16 and optionally at least one second gelling agent in the continuous phase 18, each element 14 further comprising a shell, in particular formed by a layer of coacervate at the interface between the first phase 16 and the continuous phase 18 by interaction between at least one polymer initially contained in the first phase 16 and at least one second polymer initially contained in the continuous phase 18. This variant is advantageous in that it leads to a still further improved kinetic stability of the dispersion 12.

Production Device 10

The device 10 comprises a production nozzle 20 able to form a fluid jet 22, a mechanical fragmentation device 24 intended to mechanically split the fluid jet 22 and preferably a chamber 26 intended to contain and discharge the dispersion 12.

The nozzle 20 comprises at least a first duct 30, a second duct 32 and an outlet 34, defined in a housing 35 bearing the nozzle 20.

"Fluid jet" refers to the flow of several fluids in a laminar state along a common direction, and in particular a flow in which the fluids flow while forming successive cylindrical layers, preferably concentric, arranged one around the other.

The first duct 30 and the second duct 32 each comprise a series of at least one substantially cylindrical duct segment in the frame 35.

The first duct 30 is intended to convey a first fluid 36, able to form the first phase 16, from a first supply channel 38 supplying first fluid 36. The first duct 30 emerges in the second duct 32, for example halfway along the length of the second duct 32. The segment of the first duct 30 emerging in the second duct extends along a flow axis X-X'.

According to one specific embodiment (not shown), the second duct 32 and the first duct 30 emerge at the outlet 34 of the nozzle 20 in a same plane.

The second duct 32 is intended to convey a second fluid 40, able to form the second phase 18, from a second supply channel 42 supplying second fluid 40. The second duct 32 emerges at the outlet 34 of the nozzle 20, and surrounds, preferably coaxially, part of the first duct 30 over a part of the length of the second duct 32.

The segment of the second duct 32 emerging at the outlet 34 extends along the flow axis X-X'.

The nozzle 20 is thus able to form the fluid jet 22 by coextrusion at the outlet 34, the second fluid 40 surrounding, preferably coaxially, the first fluid 36 in the fluid jet 22. The fluid jet 22 flows in the vicinity of the outlet 34 along a direction substantially parallel to the flow axis X-X'.

One skilled in the art will know how to make the necessary adjustments, in particular in terms of the flow rates of first fluid 36 and second fluid 40, to ensure the formation of the fluid jet at the outlet 34 of the nozzle 20.

The outlet 34 is an opening in the housing 35, preferably emerging in the chamber 26. The opening 34 fits in an opening plane substantially orthogonal to the flow axis X-X'.

The mechanical fragmentation device 24 is positioned in the vicinity of the outlet 34 of the nozzle 20, and comprises a mobile part 50 relative to the nozzle 34 and an actuator (not shown) intended to set the mobile part 50 in motion.

The mobile part 50 is able to split the fluid jet 22 mechanically, that is to say, the movement of the mobile part 50 cuts the fluid jet 22, preferably regularly, to divide it mechanically. The splitting of the fluid jet 22 takes place in one operation, and over a very short duration, which makes it possible to control the mechanical fragmentation action as well as the size of the elements 14.

The mobile part 50 has through openings 52 along the flow axis X-X', advantageously regularly spaced apart from one another.

According to one particular embodiment, the through openings 52 have different sizes and/or surfaces from one another. This particular embodiment for example makes it possible to form dispersions according to the invention comprising at least two populations of dispersed elements of different sizes, which can affect the desired visual and/or sensoriality and/or homogeneity of the effect, in particular cosmetic.

For example, the mobile part 50 is in the form of a flat or cylindrical grid, comprising alternating bars or wires, in particular metal, and openings 52.

Each opening 52 advantageously has a transverse expanse substantially equal to a transverse expanse of the opening 34, in a plane orthogonal to the flow axis X-X'. Thus, the opening 52 is suitable for allowing the flow of the fluid jet 22 when it is located across from the outlet 34.

The actuator is intended to set the mobile part 50 in motion along a direction substantially transverse to the flow direction of the fluid jet 22 through the outlet 34. The actuator for example comprises an electric motor and a connecting rod-crank system.

The mobile part 50 is thus mobile at least between a closed position, in which the outlet 34 is not across from one of the openings 52 and the mobile part 50 is substantially in the flow axis X-X' of the fluid jet 22, and an open position, in which the outlet 34 is across from one of the openings 52 and the mobile part 50 allows the flow of the fluid jet 22 without splitting of the latter.

The actuator is configured to move the mobile part 50 between the open position and the closed position at a predetermined frequency, so as to split the fluid jet 22 and thus form the dispersion 12 according to the invention.

The movement speed (or frequency) of the mobile part 50 between the open position and the closed position, the dimensions of the mobile part 50 and/or of the opening 52, the spacing between the mobile part 50 and the opening 52 and/or the flow rates imposed on the first fluid 36 and the second fluid 40 determine the size of the elements 14.

According to one preferred embodiment, the elements 14 are monophasic and comprise only the first fluid 36, and optionally a shell 16A as previously mentioned.

The volume of the elements 14 depends on the movement frequency of the mobile part 50, the dimensions of the mobile part 50 and/or of the opening 52, the spacing between the mobile part 50 and the opening 52 and/or the flow rates imposed on the first fluid 36 and the second fluid 40, and therefore on the fluid jet 22. In particular, the volume ratio of the elements 14 and the continuous phase 18 depends on the ratio of the flow rates of the first fluid 36 and the second fluid 40 at the outlet 34 of the nozzle 20.

The adjustments to the level of these different parameters depend on the general knowledge of the person skilled in the art. In other words, one skilled in the art will know how to make the necessary adjustments to form elements 14 having the desired size, or to manufacture a dispersion according to the invention comprising at least two populations of dispersed elements of different sizes.

The chamber 26 is intended to receive the dispersion 12 resulting from the splitting of the fluid jet 22 and to discharge the dispersion 12 for distribution.

According to a first variant (shown in FIG. 1), the chamber 26 is located directly at the outlet 34 of the nozzle 20, such that the nozzle 20 emerges directly in the receptacle 26 through the fragmentation device 24.

As illustrated in FIG. 1, the device 10 further comprises at least one mixer 71 in which the dispersion 12 is injected, able to exert a controlled and homogeneous shear on the elements 14. The mixer 71 comprises at least one shear cell.

The mixer 71 is able to improve the monodispersity of the elements 14, the elements 14 being subject to the shear capable of splitting them into elements 14 of homogeneous and controlled diameter, as described in more detail in EP3144058. According to this embodiment, the obtained dispersion 12 comprises elements 14 provided with a homogeneity of improved size.

The shear cell is advantageously a cell of the Couette type, comprising at least two coaxial rotary cylinders. The cylinders for example comprise an outer cylinder 72 having an inner radius Ro and an inner cylinder 73 having an outer radius Ri, with Ro>Ri. The outer cylinder 72 is for example stationary, and the inner cylinder 73 is for example driven in a rotational movement at a constant angular speed ω. The dispersion 12 is positioned between the outer cylinder 72 and the inner cylinder 73, and sheared by the differential movement of the two cylinders.

In a variant, the shear cell comprises two parallel rotary discs, or two parallel oscillating plates.

Other Embodiments of the Device 10

Figure 2:
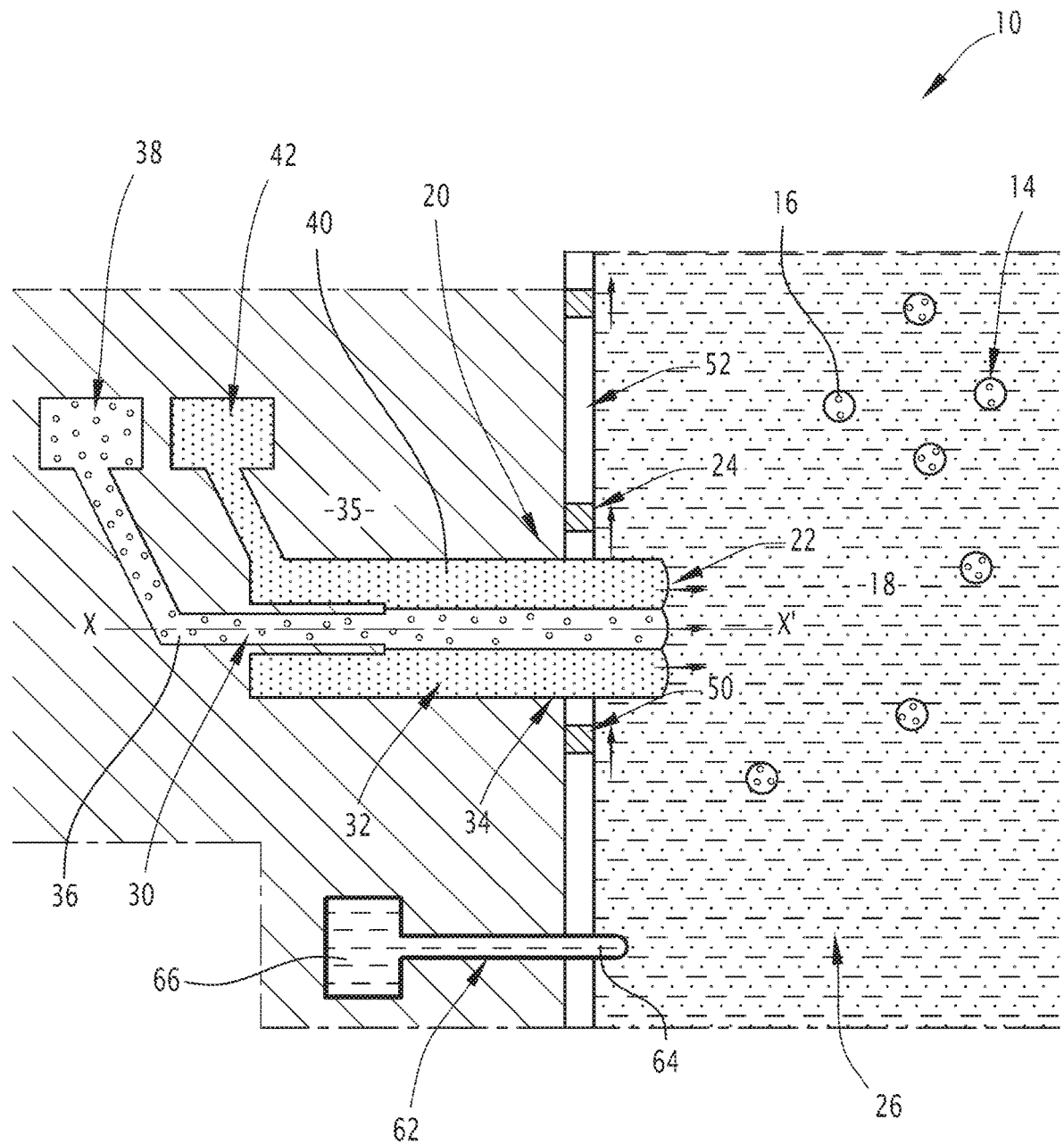
FIG. 2 is a schematic longitudinal sectional view of a second production device according to the invention.

According to one embodiment shown in FIG. 2, the device 10 further comprises at least one independent duct 62 able to convey, at the dispersion 12, at least one additional fluid 64 from an independent channel 66 supplying additional fluid 64 comprising at least one solution increasing the viscosity of the continuous phase 18. The second fluid 40 is therefore miscible with the additional fluid 64. Such a solution for increasing the viscosity is for example a solution containing a base, in particular an alkaline hydroxide, such as sodium hydroxide, and is in particular described in WO2015055748, the content of which is incorporated by reference.

Figure 3:
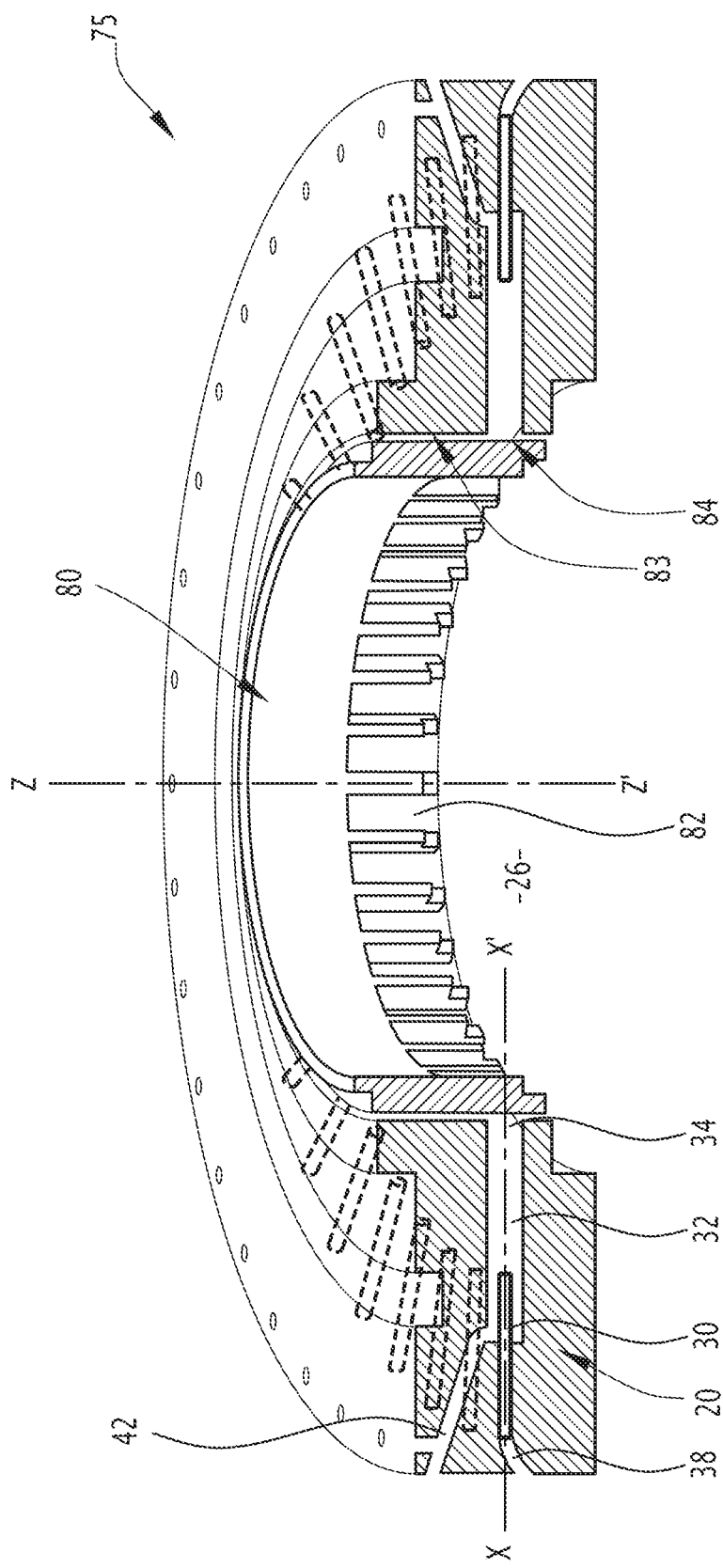
FIG. 3 is a perspective view of a production assembly according to the invention comprising a plurality of production devices.

According to another embodiment shown in FIG. 3, the mobile part of the fragmentation device 24 comprises a rotary scraper 80 rotatable about a central axis Z-Z' at a constant angular speed.

The scraper 80 is for example a rotor with a hollow shaft, substantially circular, and has openings 82 that are oriented radially, emerging on an outer contour 84 of the scraper 80. The openings 82 emerge in the hollowed central part of the scraper 80. Advantageously, the openings 82 are evenly spaced along the outer contour 84.

The outer contour 84 extends in the vicinity of the outlet 34, and is orthogonal to the flow axis X-X', such that the outer contour is substantially tangent to the plane of the opening 34.

The fragmentation device 24 is thus mobile by rotation about the central axis Z-Z' between the open position in which one of the openings 82 is across from the outlet 34 and the closed position, as described above.

The actuator is for example an electric motor able to rotate the rotary scraper about the central axis Z-Z'. The passage frequency from the closed position to the open position then depends on the angular rotation speed of the scraper 80 and the angular gap separating two successive openings 82.

In a variant, the scraper 80 is driven in an oscillating movement rather than a rotary one, preferably at a constant angular speed.

Figure 4:
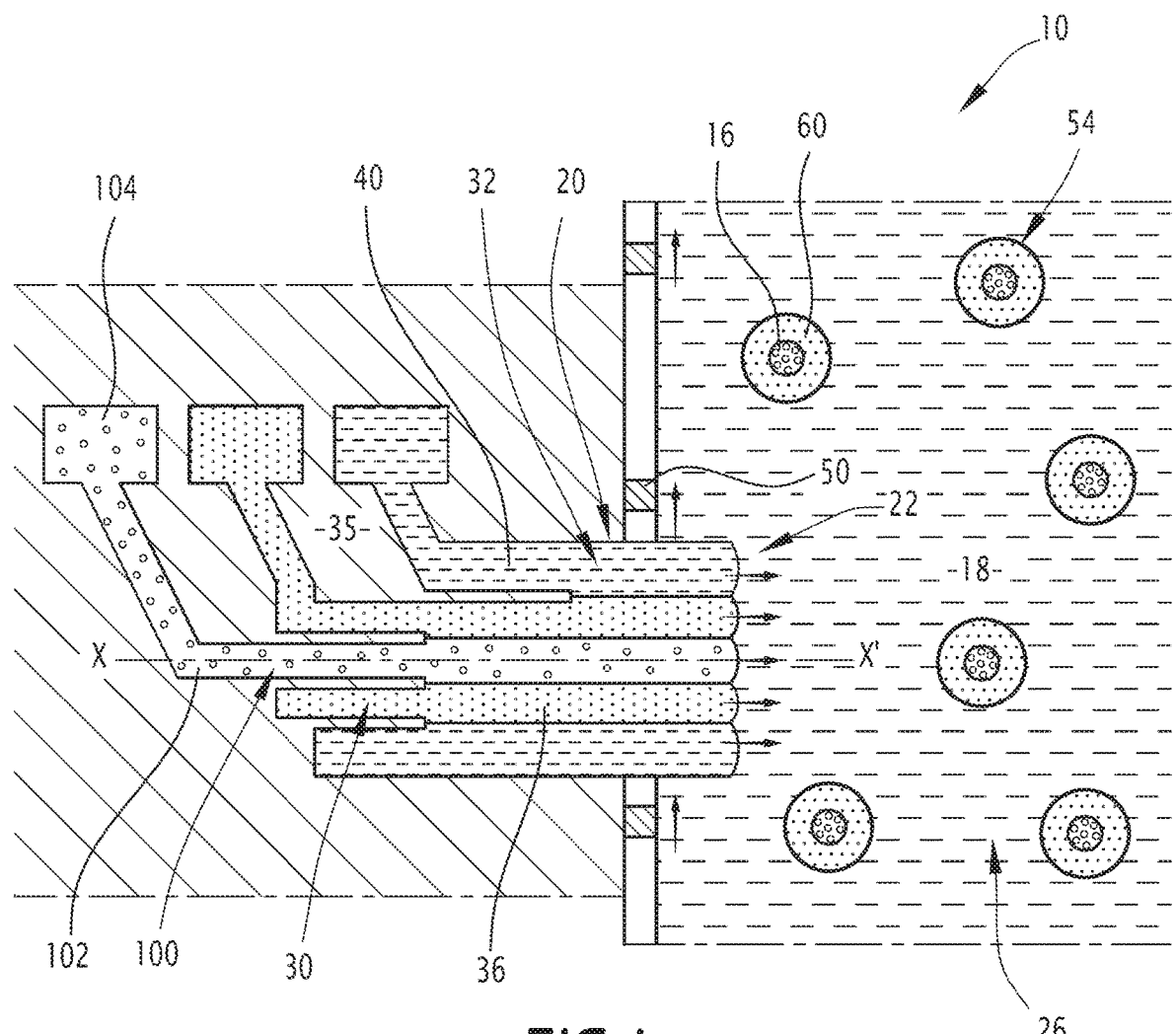
FIG. 4 is a view similar to FIG. 1 of a production device according to the invention.

According to another embodiment illustrated in FIG. 4, the device 10 comprises a nozzle 20 comprising the first duct 30 and the second duct 32 as well as a third duct 100. At least part of the third duct 100 is surrounded, preferably coaxially, by at least a part of the first duct 30. The third duct 100 is able to convey a third fluid 102, supplied by a third channel 104 supplying third fluid 102.

According to a variant (not shown), the first duct 30 and the third duct 100, or even further the second duct 32, emerge on a same plane, in particular at the outlet 34 of the nozzle 20.

The fluid jet 22 then comprises the first fluid 36, the second fluid 40 surrounding the first fluid 36, preferably coaxially, and the third fluid 102 surrounded by the first fluid 36, preferably coaxially, the fluid jet 22 being formed by coextrusion. Each of the elements 14 formed after splitting of the fluid jet 22 then comprises, at least temporarily, an outer core 110 formed by the first fluid 36, and at least one, preferably only one, inner core 112 formed by the third fluid 102, arranged in the outer core 110.

Indeed, according to a first variant, the third fluid 102 and the first fluid 36 are substantially miscible. This variant is advantageous in that it allows the encapsulation within a same phase of raw materials that are not compatible with one another, or are even of a nature to affect the proper working of the device 10.

Within the meaning of the present invention, "substantially miscible" is meant to designate the solubility of a first phase (or fluid) in a second phase (or fluid) that, at ambient temperature and atmospheric pressure, is advantageously greater than 5% by weight.

Thus, as an illustration of this first variant, in the case where the elements 14 comprise a coacervate shell 16A, the third fluid 102 comprises high content levels in plant oils and the first fluid 36 comprises at least one precursor lipophilic cationic polymer of the coacervate, in particular an amodimethicone, as previously described, in an oil known to be a good solvent of the cationic polymer. Thus, any incompatibility between said cationic polymer and the plant oil occurs after the formation of the coacervate shell.

More generally, the third fluid 102 and the first fluid 36 each comprise active ingredients that are able to react with one another; thus, these active ingredients react together after the formation of the elements 14.

This makes it possible to form monophasic elements 14.

According to a second variant, the third fluid 102 and the first fluid 36 are substantially immiscible. The dispersion 12 is thus multiple, in particular double, and in particular of the water-in-oil-in-water, oil-in-water-in-oil or oil-in-oil-in-water type. This makes it possible to form diphasic elements 14.

Figure 5:
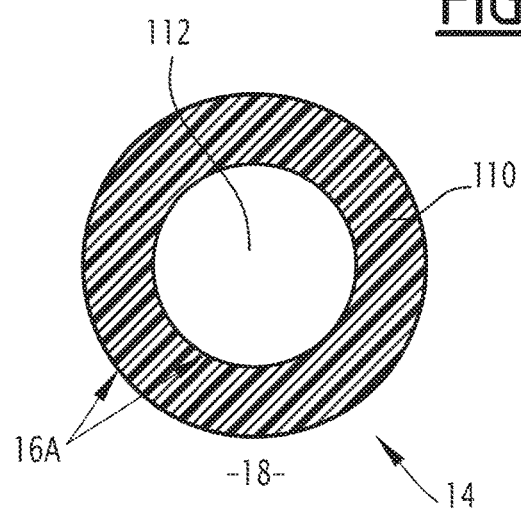
FIG. 5 is a view of an exemplary dispersion according to the invention where the elements of the dispersion are in the form of drops formed by a device according to the invention.

According to a first example, the diphasic elements 14 form drops provided with a multicomponent core, that is to say, comprising an inner core 112 formed by the third fluid 102 and an outer core 110 formed by the first fluid 36 completely surrounding the inner core 112. Optionally, these drops comprise a shell, in particular a coacervate shell, as previously described at the interface between the first fluid 36 and the continuous phase 18, or even further between the first fluid 36 and the third fluid 102. Such a drop is illustrated in FIG. 5.

According to a second example (not shown) in which the elements 14 are diphasic, the dispersion 12 is such that the first phase 16 comprises at least one first gelling agent and optionally the continuous phase 18 comprises at least one second gelling agent. In other words, the diphasic elements 14 according to this second variant have an improved kinetic stability and mechanical strength despite the absence of shell and the gelling of the outer core 110 makes it possible to avoid the creaming or sedimentation of the inner core 112. Examples of gelling agents are described in the application filed under no. FR1752208, the content of which is incorporated by reference.

According to a third example, the elements 14 form drops based on a combination of the first and second examples above.

Figure 6:
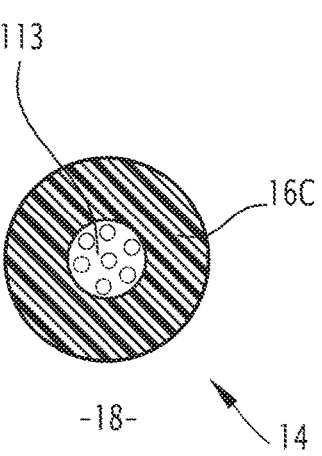
FIG. 6 is a view of an exemplary dispersion according to the invention where the elements of the dispersion are in the form of capsules formed by a device according to the invention.

According to a fourth example, the elements 14 form capsules comprising a core 113 formed by the third fluid 102 and a shell 16C formed by the first fluid 36 positioned around the core 113. Such a capsule is illustrated in FIG. 6.

The shell can be made from at least one gelling agent.

Such a gelling agent can for example be chosen from a heat-sensitive gelling agent that is solid at ambient temperature and atmospheric pressure, for example agar, and/or be chosen from a polysaccharide, in particular a polyelectrolyte that is reactive to multivalent ions, for example an alginate.

The gelling of the polyelectrolyte requires the presence in the second fluid 40 of at least one reagent able to react with the polyelectrolyte to cause it to go from a liquid state to a gelled state. Such a reagent is typically a solution comprising multivalent ions such as ions of an alkaline earth metal for example selected from calcium ions, barium ions, magnesium ions and mixtures thereof. Examples of gelling agents, in particular heat-sensitive, polysaccharides, in particular polyelectrolytes reactive to multivalent ions, and reagents able to react with the polyelectrolyte to cause it to go from a liquid state to a gelled state are described in WO2010063937.

Preferably, when the second fluid 40 comprises at least one reagent able to react with the polyelectrolyte present in the first fluid 36 to cause it to go from a liquid state to a gelled state, the first fluid 36 and/or the second fluid 40 further comprises at least one gelling retarder, for example a tetrasodium pyrophosphate.

As illustrated in FIG. 1, the device 10 further comprises at least one heating device 70 able to heat at least the first fluid 36 and/or the second fluid 40, for example at the supply channel 38 supplying first fluid 36 and/or the supply channel 42 supplying second fluid 40 and/or in the nozzle 20. The heating device 70 is for example positioned in the vicinity of the first duct 30 and/or the second duct 32, and in particular surrounds the first duct 30 and/or the second duct 32, preferably coaxially. According to a first variant, the heating device 70 for example comprises a heating resistance and an electric generator, and is able to heat the first fluid 36 and/or the second fluid 40 by Joule effect. According to a second variant, the heating device 70 for example comprises a heat exchanger.

In a variant, the heating device is able to heat the third fluid 102, and is arranged in the vicinity of the third supply channel 104 for supplying third fluid 102 and/or the third duct 100, or is able to simultaneously heat the first fluid 36, the second fluid 40 and the third fluid 102 and located in the vicinity of the first duct 30, the second duct 32 and the third duct 100.

Production Assembly 75

In reference to FIG. 3, a production assembly 75 is described comprising a plurality of production devices 10 according to the first embodiment previously described.

The production devices 10 are arranged around at least one centripetal circle, with their respective flow axes X-X' converging toward the center of the circle. In the example shown in FIG. 3, the production devices 10 are arranged along a centripetal circle, the center of which is located on the central axis Z-Z'.

According to one embodiment that is not shown, the production devices 10 are arranged along at least two superimposed centripetal circles, the centers of which are aligned along the central axis Z-Z'. Such an embodiment is advantageous in that it makes it possible to easily increase the dispersion production yields 12 according to the invention, if applicable without multiplying the supply ducts 38, 42 and optionally 104, respectively, for fluids 36, 40 and 102.

The outlets 34 of the devices 10 emerge in the same shared chamber 26, intended to receive the dispersion 12 produced by each of the devices 10.

The production assembly 75 comprises a fluid distribution system able to supply each production device 10 with first fluid 36, second fluid 40, and optionally third fluid 102, respectively by means of first channels 38, second channels 42 and optionally third channels 104.

Advantageously, the devices 10 share a same first channel 38 and a same second channel 42, and optionally a same third channel 104, the first channel 38 and the second channel 42, and optionally the third channel 104 being substantially circular and concentric with the centripetal circle.

Advantageously, each first channel 38 emerges in the first duct(s) 30 and each second channel 42 emerges in the second duct(s) 32, or even each third channel 104 emerges in the third duct(s) 100 through at least one head loss, for example formed by a channel portion of reduced section. The head loss causes a slowing of the flow of the first fluid 36, respectively of the second fluid 40, or even of the third fluid 102 upstream from the nozzle 20.

The channel portions have a section in a plane transverse to the direction of flow of the first fluid 36, respectively of the second fluid 40, or even of the third fluid 102, with a smaller area than the cross-sections of the first channel 38 and the first duct 30, respectively of the second channel 42 and the second duct 32, or even of the third channel 104 and the third duct 100. Owing to the produced head loss, it is possible to regulate the flow of the first fluid 36, respectively of the second fluid 40, or even of the third fluid 102 downstream from the head loss and to thus homogenize the fluid(s) injected into the production devices 10.

The fluid distribution system for example comprises a first pump fluidly connected to the first channel 38 and to a first fluid reservoir 36. The first pump is able to circulate the first fluid 36 in the first channel 38 and to supply the devices 10 with first fluid 36 with a predetermined flow rate.

The fluid distribution system also comprises a second pump fluidly connected to the second channel 42 and to a second fluid reservoir 40. The second pump is able to circulate the second fluid 40 in the second channel 42 and to supply the devices 10 with second fluid 40 at a predetermined flow rate, which may or may not be equal to the flow rate of the first fluid 36.

Optionally, the fluid distribution system also comprises a third pump fluidly connected to the third channel 104 and to a third fluid reservoir 102. The third pump is able to circulate the third fluid 102 in the third channel 104 and to supply the devices 10 with third fluid 102 at a predetermined flow rate, which may or may not be equal to the flow rate of the first fluid 36 and/or of the second fluid 40.

The devices 10 advantageously share the same fragmentation device, which comprises a rotary scraper 80 as described above. The rotary scraper 80 is arranged to travel an inner contour 83 of the centripetal circle and thus to be substantially tangent to the opening plane of each of the outlets 34 of the devices 10. The inner contour 83 of the centripetal circle and the outer contour 84 of the scraper 80 are advantageously separated by a distance of less than or equal to 1 mm, preferably less than or equal to 0.5 mm, and better still less than or equal to 0.2 mm.

The openings 82 of the rotary scraper 80 are advantageously evenly angularly spaced apart, the rotary scraper is therefore suitable for splitting the fluid jets 22 formed by each of the nozzles 20 at a same predetermined frequency and thus forming the elements 14 identically at the outlet 34 of each of the nozzles 20.

The openings 82 of the rotary scraper 80 can also have different sizes and/or surfaces from one another, the rotary scraper then being suitable for forming at least two populations of elements 14 with different sizes.

According to one variant embodiment, the devices 10 advantageously share the same fragmentation device, which comprises an oscillating scraper 80.

According to one variant (not shown), the production devices 10 of the assembly 75 are arranged around at least one centrifugal circle, with their respective flow axes X-X' diverging from the center of the circle.

The outlets 34 of the devices 10 are oriented toward the outside of the centrifugal circle and emerge in the same substantially annular shared chamber 26, positioned around the production devices 10.

The fluid distribution system is as described above, the first channel 38, the second channel 42 and optionally the third channel 104 for fluid distribution being positioned inwardly relative to the production devices 10, for example in the vicinity of the central axis Z-Z'.

The rotary or oscillating scraper 80 is shared between the devices 10 and arranged to travel an outer contour of the centrifugal circle. An inner contour of the scraper 80 is thus substantially tangent to the outlets 34 of the devices 10, as described above.

According to a second variant (not shown), the outlets 34 of the nozzles 20 are arranged substantially parallel to one another, and substantially parallel to the central axis Z-Z'. The rotary or oscillating scraper 80 is arranged to come across from the outlets of the nozzles 20 parallel to one another.

The scraper 80 for example assumes the form of a disc rotating about the central axis Z-Z', having through openings 52 in the vicinity of its periphery, arranged to come across from the outlets 34 and emerging in the chamber 26. The scraper 80 has a thickness greater than or equal to 5 mm, in particular greater than or equal to 10 mm, or even greater than or equal to 20 mm, and preferably less than or equal to 200 mm, advantageously less than or equal to 100 mm.

Thus, the opening(s) 52 can thus assume the form of a tunnel, for example circular or oblong, which constitutes an environment favorable to producing stabilization phenomena of the dispersed elements under gentle conditions, in particular when the shell is formed by a layer of coacervate as previously described, next allowing the dispersion to better withstand the disruptions and/or shear phenomena that may occur in the chamber 26.

The fragmentation device 24 according to this second variant embodiment can further advantageously comprise at least one cooling system. Such an "integrated" and continuous cooling system has improved cooling performance levels and a spatial optimization relative to a conventional cooling system at best positioned at the chamber 26.

Production Method

A method for producing the dispersion 12 implementing the device 10 shown in FIG. 1 will now be described. The production method comprises a preliminary step for providing the production device 10, as well as a first fluid 36 and a second fluid 40 that is substantially immiscible with the first fluid 36.

Advantageously, the first fluid 36 is provided by means of a first supply channel 38 supplying first fluid 36 fluidly connected to a first duct 30 and the second fluid 40 is supplied by means of a second supply channel 42 supplying second fluid 40 fluidly connected to a second duct 32 of a nozzle 20 of the device 10.

The method comprises at least one step for pouring, toward an outlet 34 of the nozzle 20 in a flow direction X-X', the first fluid 36 in a first duct 30 and the second fluid 40 in a second duct 32, said second duct 32 surrounding, preferably coaxially, at least part of the first duct 30.

The method next comprises a step for forming a fluid jet 22 at the outlet 34 of the nozzle 20, the fluid jet 22 being formed by co-extrusion and comprising the first fluid 36 and the second fluid 40 surrounding the first fluid 36, preferably coaxially.

Advantageously, the fluid jet 22 flows in the flow direction X-X', and transverse to an opening plane of the outlet 34.

The method comprises a step for movement of a mobile part 50 of a fragmentation device 24 of the production device 10, in order to split the fluid jet 22 and obtain a dispersion 12 according to the invention.

Advantageously, the mobile part 50 is moved along a direction substantially orthogonal to the flow direction X-X', and substantially tangential to the opening plane of the outlet 34.

Advantageously, the mobile part 50 is moved by an actuator so as to form the elements 14 at a fixed predetermined frequency. The elements 14 are then substantially identical to one another, such that the obtained dispersion 12 is monodisperse.

Advantageously, the mobile part 50 is a rotary scraper 80, the movement of the mobile part 50 is then a rotation about a central axis Z-Z' at a constant angular speed. In a variant, the mobile part 50 is a scraper driven in an oscillating movement rather than a rotary one at a constant angular speed.

An outer contour 84 of the rotary scraper then extends in the vicinity of the outlet 34, substantially tangent to the opening plane of the outlet 34.

The method lastly comprises a step for recovering the dispersion 12 comprising the elements 14 dispersed in the continuous phase 18.

In another embodiment, the method comprises the step of pouring the first fluid 36 and the second fluid 40 as described above, as well as a third fluid 102 in a third duct 100 surrounded at least partially, preferably coaxially, by at least part of the first duct 30.

According to a first variant, the third fluid 102 is substantially miscible with the first fluid 36.

According to a second variant, the third fluid 102 is substantially immiscible with the first fluid 36.

The fluid jet 22 thus formed by coextrusion comprises the first fluid 36, the second fluid 40 and the third fluid 102, in which the second fluid 40 surrounds the first fluid 36, preferably coaxially, and the first fluid 36 surrounds the third fluid 102, preferably coaxially.

In the dispersion 12 thus obtained and depending on the miscible or immiscible nature of the first fluid 36 and third fluid 102 relative to one another, the elements 14 are monophasic or diphasic.

In another embodiment, the method further comprises a size refining step, during which a controlled and homogeneous shear is applied to the elements 14 in a mixer, the mixer in particular being as previously described.

In another embodiment, the method further comprises a step for filtration of the dispersion 12 to collect only the elements 14.

Additional Compounds and Active Ingredients

A dispersion 12 according to the invention, in particular the dispersed phase 16 (first fluid 36) and/or the continuous phase 18 (second fluid 40) and/or the third fluid 102, can further comprise at least one additional compound that is different from the precursor polymers of the aforementioned coacervate, gelling agents and polysaccharides.

A dispersion 12 according to the invention, in particular the dispersed phase 16 (first fluid 36) and/or the continuous phase 18 (second fluid 40) and/or the third fluid 102, can further comprise powders, flakes, dyes, in particular selected from water-soluble or non-water-soluble, liposoluble or non-liposoluble, organic or inorganic dyes, pigments, materials with optical effects, liquid crystals, and mixtures thereof, particulate agents that are insoluble in the fatty phase, emulsifying and/or non-emulsifying silicone elastomers, preservatives, humectants, stabilizers, chelating agents, emollients, modifiers selected from pH, osmotic force and/or refraction index modifying agents, etc., or any typical cosmetic additive, and mixtures thereof.

A dispersion 12 according to the invention, in particular the dispersed phase 16 (first fluid 36) and/or the continuous phase 18 (second fluid 40) and/or the third fluid 102, can further comprise at least one active ingredient, in particular biological or cosmetic, preferably chosen from hydrating agents, healing agents, depigmenting agents, UV filters, peeling agents, antioxidant agents, agents stimulating the synthesis of dermal and/or epidermal macromolecules, dermo-relaxing agents, anti-perspirant agents, soothing agents, anti-aging agents, perfuming agents and mixtures thereof. Such active ingredients are in particular described in FR 1,558,849, the content of which is incorporated by reference.

Of course, one skilled in the art will be sure to choose any of the aforementioned additional compound(s) and/or the respective quantities thereof such that the device and/or the advantageous properties of a dispersion according to the invention are not or are substantially not altered by the considered addition. In particular, the nature and/or quantity of the additional compound(s) depend on the aqueous or oily (or fatty) nature of the considered phase of the dispersion according to the invention. These adjustments are within the skills of one skilled in the art.

Uses

A dispersion according to the invention can be a topical, and therefore not oral, composition, or a dietary composition.

Preferably, a dispersion according to the invention is usable directly, at the end of the aforementioned preparation methods, as a composition, in particular cosmetic.

The dispersions according to the invention can comprise, aside from the aforementioned ingredients, at least one physiologically acceptable medium.

In the context of the invention, and unless otherwise mentioned, "physiologically acceptable medium" refers to a medium appropriate for cosmetic applications, and in particular suitable for the application of a composition according to the invention on a keratinous material, in particular the skin and/or hair, and more particularly the skin.

The physiologically acceptable medium is generally suitable for the nature of the medium on which the composition must be applied, as well as the appearance under which the composition must be conditioned.

According to one embodiment, the physiologically acceptable medium is configured directly by the continuous phase as described above.

The cosmetic compositions according to the invention can for example be a cream, an emulsion, a lotion, a serum, a gel and an oil for the skin (hands, face, feet, etc.), a foundation (liquid, paste), a preparation for baths and showers (salts, foams, oils, gels, etc.), a haircare product (hair colors and bleaches), a cleaning product (lotions, powders, shampoos), a hair maintenance product (lotions, creams, oils), a hair-styling product (lotions, lacquers, brillantines), a shaving product (soaps, foams, lotions, etc.), a product intended to be applied on the lips, a sun product, a sunless tanning product, a product making it possible to whiten the skin, an anti-wrinkle product. In particular, the cosmetic compositions according to the invention can be an antiaging serum, a youth serum, a hydrating serum or a perfumed water.

The present invention also relates to a non-therapeutic method for cosmetic treatment of a keratinous material, in particular the skin and/or the hair, and more specifically the skin, comprising a step for applying, on said keratinous material, at least one composition or at least one layer of a cosmetic composition as mentioned above.

Throughout the disclosure, the expression "comprising a" must be understood as being synonymous with "comprising at least one," unless otherwise specified.

The expressions "between . . . and . . . ," "from . . . to . . . " and "ranging from . . . to . . . " must be understood as being inclusive, unless otherwise specified.

What is claimed is:

1. A device for producing a dispersion comprising elements comprising at least one first phase, which are dispersed in a continuous phase substantially immiscible with the first phase, the device comprising:
   at least one production nozzle comprising at least a first duct intended to convey a first fluid that forms the first phase, a second duct surrounding at least part of the first duct, the second duct being able to convey a second fluid that forms the continuous phase, and an outlet, the nozzle being able to form, at the outlet, a fluid jet comprising at least the first fluid and the second fluid surrounding the first fluid and
   at least one fragmentation device for mechanically breaking up the fluid jet, positioned in the vicinity of the outlet of the nozzle, the fragmentation device comprising a mobile part relative to the nozzle, intended to break up the fluid jet mechanically into a plurality of elements comprising the first fluid dispersed in the continuous phase,
   wherein the mobile part of the fragmentation device comprises a rotating or oscillating scraper, provided with successive openings, and the mobile part is mobile at least between a closed position, in which the outlet is not across from one of the openings and the mobile part is substantially in a flow axis of the fluid jet, and an open position, in which the outlet is across from one of the openings and the mobile part allows the flow of the fluid jet without splitting of the latter.

2. An assembly for producing a dispersion comprising:
   a) a plurality of production devices for producing a dispersion comprising elements comprising at least one first phase, which are dispersed in a continuous phase substantially immiscible with the first phase, and
   b) a fluid distribution system able to supply each device at least with first fluid and second fluid, the outlets of the nozzles emerging in a same chamber,
   each production device comprising:
      at least one production nozzle comprising at least a first duct intended to convey a first fluid that forms the first phase, a second duct surrounding at least part of the first duct, the second duct being able to convey a second fluid that forms the continuous phase, and an outlet, the nozzle being able to form, at the outlet, a fluid jet comprising at least the first fluid and the second fluid surrounding the first fluid, and
      at least one fragmentation device for mechanically breaking up the fluid jet, positioned in the vicinity of the outlet of the nozzle, the fragmentation device comprising a mobile part relative to the nozzle, intended to break up the fluid jet mechanically into a plurality of elements comprising the first fluid dispersed in the continuous phase,
   the production devices being positioned along at least one centripetal circle, the outlets of the nozzles being oriented toward a center of the circle.

* * * * *